United States Patent [19]

Araki et al.

[11] Patent Number: 5,475,183
[45] Date of Patent: Dec. 12, 1995

[54] PROCESS FOR PRODUCING LOWER OLEFINS

[75] Inventors: Shintaro Araki; Katsuo Taniguchi; Toshiyuki Isaka, all of Yamaguchi, Japan

[73] Assignee: Mitsui Petrochemical Industries, Ltd., Japan

[21] Appl. No.: 161,061

[22] Filed: Dec. 3, 1993

Related U.S. Application Data

[63] Continuation of Ser. No. 826,765, Jan. 28, 1992, abandoned.

[30] Foreign Application Priority Data

Feb. 4, 1991 [JP] Japan ..................................... 3-013516
Mar. 29, 1991 [JP] Japan ..................................... 3-066062

[51] Int. Cl.[6] ........................................................ C07C 1/20
[52] U.S. Cl. ............................................ 585/640; 583/638
[58] Field of Search ..................................... 585/640, 638

[56] References Cited

FOREIGN PATENT DOCUMENTS 0379803 of 1990 European Pat. Off. .
3017501 of 1980 Germany .
64-34929 2/1989 Japan .

OTHER PUBLICATIONS

Chemical Abstracts vol. 111, No. 24, 2150860, Dec. 1989.

*Primary Examiner*—Asok Pal
*Attorney, Agent, or Firm*—Nixon & Vanderhye

[57] ABSTRACT

A process for the production of lower olefins by dehydrating lower alcohols having 2 to 4 carbon atoms which comprises using a γ-alumina catalyst containing 0.3% by weight or less of impurities in total excluding $SiO_2$, the impurities including 0.2% by weight or less of sulfur content calculated in terms of $SO_4-$ and 0.05% by weight or less of sodium content calculated in terms of $Na_2O$, and/or a process for the production of lower olefins by dehydrating lower alcohols having 2 to 4 carbon atoms that comprises using a γ-alumina catalyst which contains 0.5 to 5% by weight of $SiO_2$.

According to the process of the present invention, lower olefins can be produced from lower alcohols with high yield and high selectivity for a prolonged period of time without reducing the catalytic activity.

3 Claims, No Drawings

PROCESS FOR PRODUCING LOWER OLEFINS

CROSS-REFERENCE TO RELATED APPLICATIONS

This application is a continuation of earlier application Ser. No. 07/826,765, filed Jan. 28, 1992, abandoned.

FIELD OF THE INVENTION

This invention relates to a process for the production of lower olefins from lower alcohols having 2 to 4 carbon atoms, by dehydrating the alcohols using specified catalysts.

BACKGROUND OF THE INVENTION

Various processes have been proposed for the production of high purity olefins by means of dehydration of alcohols, for example, a process in which ethylene is produced by dehydrating ethanol in the presence of solid acid catalysts such as alumina, silica, silica-alumina, zeolites, solid phospholic acid and the like (Japanese Patent Application Kokai No. 64-34929).

When dehydration is carried out using a solid acid as a catalyst, it is necessary to keep the reaction temperature at 250° to 300° C. or higher because of the great endothermic alcohol dehydration reaction. In addition, application of solid acid catalysts such as silica alumina, zeolites, solid phosphoric acid and the like is not desirable, because their strongly acidic nature causes decrease in the yield of olefins due to heavy materials formed by polymerization of the formed olefins, and the heavy material thus formed adheres no the catalyst surface and decreases the catalytic activity.

In such an instance, γ-alumina may be used advantageously, because its weakly acidic nature does not entail polymerization and the like of formed olefins. However, the catalytic activity of γ-alumina decreases greatly for a prolonged period of time. That is a significant drawback for using γ-alumina to produce olefins.

It is known generally that 7-alumina is transformed into α form under high pressure or at a high temperature off 1000° C. or more and that such a transition can be prevented by the addition of a metal oxide as a secondary component such as $La_2O_3$, MgO, $SiO_2$ or the like. However, it is difficult to apply such a prior arm means for the prevention of high temperature crystal phase transition to a reaction system at a low temperature of around 300° C. under a low pressure, because nothing is known about the phenomenon or mechanism of crystal phase transition under such conditions.

Though it is possible to effect the hydration reaction without pressurization, such an operation requires complex handling because of the necessity to set additional process steps and is disadvantageous also from the economical point of view. That is, being gaseous under ambient temperature and pressure, lower olefins having 2 to 4 carbon atoms formed by the reaction must be liquefied prior to their purification by distillation or the like which requires cooling using a refrigerating machine or pressurization using a compressor.

In view of the above, it therefore becomes a primary object of the present invention to provide a process by which Lower olefins can be produced from lower alcohols with high yield and high selectivity for a prolonged period of time using simple equipments.

SUMMARY OF THE INVENTION

According to the present invention, there is provided a process for producing lower olefins by dehydrating lower alcohols having 2 to 4 carbon atoms which comprises using a γ-alumina catalyst containing 0.3% by weight or less of impurities in total excluding $SiO_2$, the impurities including 0.2% by weight or less of sulfur content calculated in terms Of SO— and 0.05% by weight or less of sodium content calculated in terms of $Na_2O$, and/or another γ-alumina catalyst which contains 0.5 to 5% by weight of $SiO_2$.

Also, according to the present invention, there is [provided a process for producing lower olefins by dehydrating Lower alcohols having 2 to 4 carbon atoms which comprises effecting the reaction at a temperature of from 150° to 500° C. and under such a pressure condition that formed olefins liquefy at ordinary temperature.

DETAILED DESCRIPTION OF THE INVENTION

The following describes the present invention in detail.

Alcohols to be used as the starting material of the present invention are lower alcohols each having 2 to 4 carbon atoms, including primary, secondary and tertiary alcohols such as ethanol, n-propanol, i-propanol, n-butanol and i-butanol or mixtures thereof.

It was found for the first time by the inventors of the present invention that the catalytic activity of γ-alumina decreases greatly because of the transition of a moiety of its crystal phase from γ form to α form when used in a reaction system for a long period of time under a pressurized condition even at a low temperature of from 300° to 3500° C. Since such a tendency becomes significant as the pressure level increases, it is difficult to use γ-alumina as a catalyst in an industrial process under a pressurized condition.

The present invention is characterized by the use of a specified catalyst in the dehydration reaction. The inventive catalyst is a γ-alumina catalyst which contains 0.3% by weight or less of impurities in total excluding $SiO_2$, preferably 0.1% by weight or less. Sulfur content in the impurities may be 0.2% by weight or less, preferably 0.1% by weight or less, more preferably 0.06% by weight or less, calculated in terms of $SO_4$— and sodium content in the impurities may be 0.05% by weight or less, preferably 0.03% or less, calculated in terms of $Na_2$.

When the sum total of impurities such as Na, Fe, $SO_4$ and the like ions, excluding $SiO_2$, and sulfur and sodium contents of the impurities in a γ-alumina catalyst are restricted within the aforementioned ranges, the catalyst is hardly converted into α-form and therefore its catalytic activity does not decrease even after its use in the dehydration reaction for a prolonged period of time at a temperature of from 150° to 500° C. under a pressurized condition. In addition, a γ-alumina catalyst with reduced sodium content improves yield of the dehydration reaction.

Another characteristic nature of the catalyst to be used in the present invention is that it contains $SiO_2$ in an amount of from 0.5 to 5% by weight, preferably from 0.5 to 3% by weight. When the $SiO_2$ content is restricted within this range, crystal phase transition of the catalyst from γ-form into α-form can be prevented and therefore its catalytic activity does not decrease even after its use in the dehydration reaction for a prolonged period of time at a temperature of from 150° to 500° C. under a pressurized condition.

The two features of the catalyst described above may be effected in a combined manner.

γ-Alumina may be produced by any known method, provided that its impurity and/or $SiO_2$ contents are within the aforementioned ranges. For example, it may be produced from an acidic aluminium salt by mixing aluminium sulfate with sodium aluminate or by mixing aluminium sulfate with calcium carbonate, from an organic aluminium compound by its hydrolysis or from an alumina hydrate by Bayer's process.

When produced from an aluminium salt or from an alumina hydrate by Bayer's process, it is necessary to wash the aluminium hydrate with a sufficient volume of water at the time of its filtration, in order to attain the aforementioned range of impurities in the resulting γ-alumina to be used in the present invention. In that instance, it is desirable to add ammonia to the washing water to a concentration of 0.5 to 25%, for the purpose of keeping crystal form of the hydrate. When γ-alumina is produced from an alumina hydrate obtained by Bayer's process, removal of sodium contents is not so easy. For this reason, γ-alumina once obtained by baking of the hydrate is washed with dilute aqueous solution of hydrochloric acid, acetic acid or the like and then with water to remove sodium contents. By carrying out such handling steps, amounts of impurities are reduced to predetermined levels. In order to avoid contamination of impurities, it is desirable to operate drying and baking steps in an atmosphere of nitrogen, air (pure air not including reactive gases), an inert gas or the like.

Preferably, γ-alumina may be produced by a process in which amounts of contaminated impurities can be reduced at the time of the starting material. Especially, it is preferable to employ a process in which γ-alumina is prepared from an organic aluminium compound, because such a starting material does not contain Na and $SO_4$ ions.

Examples of organic aluminium compounds to be used include aluminium isopropoxide, aluminium ethoxide, aluminium tributoxide, triethyl aluminium, triisobutyl aluminium and the like. Since trialkyl aluminium compounds are difficult to handle and dangerous because of the necessity to carry out oxidation reaction, it is preferable to use an aluminium alkoxide as the starting material. Particularly preferred is aluminium isopropoxide, because it can be purified by distillation easily due to its low boiling point and is easily available. When aluminium isopropoxide is used as the starting material, γ-alumina may be produced by hydrolyzing the starting material under a reflux condition after mixing it with isopropanol and water, washing the resulting precipitate with aqueous ammonia and then subjecting the washed precipitate to baking. Baking may be effected at such a temperature level that the product becomes γ-form, preferably within the range of from 550° to 650° C.

On the other hand, for the purpose of including a predetermined amount of $SiO_2$ in γ-alumina, $SiO_2$ is added during the production process of γ-alumina or at the time of its use as a catalyst.

Addition of $SiO_2$ may be carried out during any one step or steps of the production process of γ-alumina. For example, an $SiO_2$ source may be added to boehmite, pseudo-boehmite or the like which is a starting material of γ-alumina, or to aluminium sulfate, sodium aluminate or the like at the time of material preparation. Also, it may be added to γ-alumina powder as a final product. In order to satisfy the effect of its addition, it is necessary to disperse $SiO_2$ in γ-alumina to a certain extent of uniformity. Any source of $SiO_2$ may be used, provided that it becomes the form of $SiO_2$ finally. For example, the $SiO_2$ source may be added as hydrogel or hydrosol of $SiO_2$ or as an alkyl compound such as ethylsilicate.

It is desirable to prevent γ-alumina from contamination of other metal oxides such as $La_2O_3$, $MgO$ and the like, because the presence of such compounds deteriorates the catalyst quickly though they are known to have an effect to prevent transition into α-form at a high temperature.

With regard to other physical properties of γ-alumina, though not particularly limited, it may preferably have a mean pore size of from 50 to 150 Å and a specific surface area of from 100 to 350 $m^2$/g.

The catalyst may be made into a powder form or a granular form, or used as a fixed bed by making it into pellet form by means of tablet molding. Though not particularly required, the catalyst may be subjected to pretreatment such as baking treatment.

Olefins to be produced by the process of the present invention include ethylene, propylene, 1-butene, 2-butene and isobutene, preferably ethylene, propylene and isobutene.

Preferred dehydration reaction conditions according to the process of the present invention are as follows. The reaction temperature may be in the range of from 150° to 500° C., preferably from 250° to 400° C. The reaction progresses with high yield within this temperature range, thus rendering possible industrial scale production. The reaction may be carried out under reduced, normal or pressurized pressure condition. However, taking the aforementioned purification-related problem into consideration, it is preferable to carry out the reaction under such a pressurized condition that formed olefins liquefy at ordinary temperature. The starting material may be fed into a reaction vessel at a rate of from 0.1 to 20 $hr^{-1}$, preferably from 0.5 to 10 $hr^1$, in terms of LHSV (liquid hourly space velocity). Feeding rate if smaller than this range would result in low productivity, thus requiring a large equipment, and if larger than this range would result in low reaction yield, thus requiring additional energy for separation and recovery of the resulting product. Feeding rates outside this range, therefore are not economical.

According to the process of the present invention, a gaseous material inert to the dehydration reaction may be used in order to discharge olefins formed by the reaction quickly from the reaction system. Examples of such gaseous materials include nitrogen, helium, argon, methane, ethane, propane, butane and the like. In this instance, it is preferable to avoid the presence of water because of a possibility of enhancing crystal phase transition due to the presence of water. Also useful as the gaseous materials are those which are liquid before their feeding in a reactor but become gaseous form under reaction conditions inside the reactor. Examples of such materials include: aliphatic hydrocarbons such as pentane, hexane, heptane, cyclopentane, cyclohexane and the like; and aromatic hydrocarbons such as benzene, toluene, xylene, ethylbenzene, cumene and the like.

When the gaseous material is fed into a reactor vessel by mixing it with an alcohol, it may be used preferably in an amount of from 0.05 to 10 moles per 1 mole of the alcohol. When the gaseous material is used in larger amounts than this range, it is necessary to recycle the gaseous material by separating it from a mixture of an olefin with water as the reaction products, thus entailing economical disadvantages such as high production cost of olefins.

According to the process of the present invention, the reaction may be carried out preferably in a continuous manner. As to the type of the reactor, it is preferable to employ a fixed bed system in which a catalyst is used in granular form.

EXAMPLES

The following inventive and comparative examples are provided to further illustrate the present invention. It is to be understood, however, that the examples are for purpose of illustration only and are not intended as a definition of the limits of the invention. In this instance, crystal phase transition of γ-alumina catalyst was checked by the following simple means.

(Steam Resistance Test of Catalyst)

A 1 to 50 g portion of a catalyst was wrapped in 200 mesh SUS 316 net and charged in a 2,000 cc capacity autoclave together with a coil-shaped filler (HELIPAK industrially available by TOKYO TOKUSHU KANAAMI K. K.) of SUS 316. In this instance, the catalyst was set in the central position. After heating to 400° C. using an electric furnace, water was fed into the autoclave using a high pressure pump and pressure in the vessel was increased to 80 kg/cm$^2$G. After 6 hours of the treatment, the catalyst was taken out and subjected to X ray analysis to examine its crystal phase. When required, the thus treated catalyst was checked for its specific surface area and its activity as a catalyst for olefin production.

(Preparation of Catalyst 1)

Commercially available reagent grade aluminium isopropoxide was mixed with isopropanol and water and subjected to hydrolysis under reflux condition. The precipitate thus formed was suspended in aqueous ammonia which has been adjusted to pH 13, and the suspension was stirred for a whole day and night. Thereafter, the thus treated precipitate was filtered, washed with water and then subjected to baking at 600° C. for 5 hours in an electric furnace. When the thus obtained alumina was analyzed, its $SiO_2$ content was found to be 0.1% by weight or less, its $SO_4-$ and $Na_2O$ contents were both 0.01% by weight or less and its purity (dry basis) was 99.9% by weight or more. When its crystal was analyzed by X-ray diffraction (XRD), no peaks other than a peak belonging to γ-form were observed. The thus obtained alumina was molded into 3 mm ×3 mm tablets.

(Preparation of Catalyst 2)

An aqueous solution of commercially available reagent grade aluminium sulfate was neutralized by mixing it with an aqueous solution of sodium aluminate to collect precipitate. The precipitate thus collected was washed with aqueous ammonia which has been adjusted to pH 13. After repeating the washing step 7 times, the precipitate was stirred for a whole day and night in aqueous ammonia which has been adjusted to pH 13. Thereafter, the thus treated precipitate was filtered, washed with water and then subjected to baking at 600° C. for 5 hours in an electric furnace. When the thus obtained alumina was analyzed, its $SiO_2$ content was found to be 0.1% by weight or less, its $SO_4-$ content was 0.1% by weight, its $Na_2O$ contents was 0.04% by weight and its purity (dry basis) was 99.8% by weight. When its crystal was analyzed by X-ray diffraction (XRD), no peaks other than a peak belonging to γ-form were observed. The thus obtained alumina was molded into 3 mm×3 mm tablets.

(Preparation of Catalyst 3)

Commercially available reagent grade aluminium isopropoxide and 2.6% by weight of ethyl silicate as a source of $SiO_2$ based on aluminium isopropoxide were dissolved in isopropanol. The thus prepared isopropanol solution was mixed with water and subjected to hydrolysis under reflux condition. The precipitate thus formed was suspended in aqueous ammonia which has been adjusted to pH 13, and the suspension was stirred for a whole day and night. Thereafter, the thus treated precipitate was filtered, washed with water and then subjected to baking at 600° C. for 5 hours in an electric furnace. When the thus obtained alumina was analyzed, its $SO_4-$ and $Na_2O$ contents as dry basis were both 0.01% by weight or less. Its $SiO_2$ content was found to be 3% by weight, with 0.1% by weight or less of impurities excluding $SiO_2$, and its purity (dry basis) was 96.9% by weight. When its crystal was analyzed by X-ray diffraction (XRD), no peaks other than a peak belonging to γ-form were observed. The thus obtained alumina was molded into 3 mm×3 mm tablet s.

(Preparation of Comparative Catalyst 1)

An aqueous solution of commercially available reagent grade aluminium sulfate was neutralized by mixing it with an aqueous solution of sodium aluminate to collect precipitate. The precipitate thus collected was stirred for a whole day and night in aqueous ammonia which has been adjusted to pH 13. Thereafter, the thus treated precipitate was filtered, washed with water and then subjected to baking at 600° C. for 5 hours in an electric furnace. When the thus obtained alumina was analyzed, its content of impurities excluding $SiO_2$ was found to be 0.9% by weight or less, with its $SiO_2$, $SO_4-$ and Na20 contents being 0.1% by weight or less, 0.6% by weight and 0.2% by weight, respectively, and its purity (dry basis) being 99.1% by weight or more. When its crystal was analyzed by X-ray diffraction (XRD), no peaks other than a peak belonging to γ-form were observed. The thus obtained alumina was molded into 3 mm×3 mm tablets.

(Preparation of Catalyst 4)

An aqueous solution of commercially available reagent grade aluminium sulfate was mixed with an aqueous solution of sodium aluminate to collect precipitate. To the precipitate thus collected was added 3% by weight of silica sol (trade name, Snowrex) based on the precipitate, and the resulting mixture was stirred for a whole day and night in aqueous ammonia which has been adjusted to pH 13. Thereafter, the thus treated precipitate was filtered, washed with water and then subjected to baking at 600° C. for 5 hours in an electric furnace. When the thus obtained alumina was analyzed, its content of impurities excluding $SiO_2$ was found to be 0.2% by weight or less, with its $SiO2$, $SO_4-$ and $Na_2O$ contents being about 2% by weight, 0.09% by weight and 0.08% by weight, respectively. The thus obtained alumina was molded into 3 mm× 3 mm tablets.

(Preparation of Comparative Catalyst 2)

Comparative catalyst 2 was prepared by repeating the procedure for the preparation of catalyst 4 except that silica sol was not used. When the thus obtained alumina was analyzed, its content of impurities excluding $SiO_2$ was found to be 0.2% by weight or less, with its $SiO_2$, $SO_4-$ and $Na_2O$ contents being 0.1% by weight or less, 0.08% by weight and 0.10% by weight, respectively.

(Preparation of Comparative Catalyst 3)

An aqueous solution of commercially available reagent grade aluminium sulfate was mixed with an aqueous solution of sodium aluminate to collect precipitate. To the precipitate thus collected was added 10% by weight of silica sol (trade name, Snowtex) based on the precipitate, and the resulting mixture was stirred for a whole day and night in aqueous ammonia which has been adjusted to pH 13. Thereafter, the thus treated precipitate was filtered, washed with water and then subjected to baking at 600° C. for 5 hours in an electric furnace. When the thus obtained alumina was analyzed, its content of impurities excluding $SiO_2$ was found to be 0.2% by weight or less, with its $Si_2$, $S_4-$ and $Na_2O$ contents being about 7% by weight, 0.10% by weight and 0.09% by weight, respectively. The thus obtained alumina was molded into 3 mm× 3 mm tablets.

(Preparation of Catalyst 5)

A commercially available γ-alumina catalyst (trade name, KHO-24; manufactured by Sumitomo Chemical Co., Ltd.) was pulverized and then mixed with 3% by weight of a commercially available silica gel (Kanto Kagaku Co., Ltd.). By adding an appropriate amount of water, the thus prepared mixture was ground using a mortar and then molded into 3 mm×3 mm tablets. When the thus obtained alumina was analyzed, its content of impurities excluding $SiO_2$ was found to be 1.1% by weight or less, with its $SiO_2$, $SO_4-$ and $Na_2O$ contents being about 2% by weight, 0.70% by weight and 0.30% by weight, respectively.

Example 1

A vertical type reaction tube made of SUS 316 (inside diameter, 25.4 mm; length, 50 cm) equipped with an external electric furnace was packed with 40 cc of the catalyst 1, and temperature of the electric furnace was increased to 320° C. Isopropanol was fed from the top of the reaction tube at an LHSV of 1 $hr^{-1}$, and the reaction was effected by increasing pressure in the reaction tube to 18 $kg/cm^2G$. A gas/liquid mixture discharged from the bottom of the reaction tube was separated into gas and liquid phases. When examined 5 hours after the commencement of the reaction, conversion of isopropanol was found to be 73 mole % and selectivity of propylene was 92 mole %. Diisopropyl ether was found as a byproduct.

Next, steam resistance of the catalyst 1 was evaluated in accordance with the procedure described above. Results of the X-ray analysis showed no transition into α-form. A 40 cc portion of the catalyst 1 after its steam resistance test was packed in the same type of the reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of isopropanol was found to be 73 mole % and selectivity of propylene was 92 mole % thus showing no changes in the catalytic activity by the steam treatment. Diisopropyl ether was found as a byproduct.

Comparative Example 1

The same type of reaction tube as used in Example 1 was packed with 40 cc of the comparative catalyst 1 prepared above, and the reaction was carried out under the same conditions as in Example 1. A gas/liquid mixture discharged from the bottom of the reaction tube was separated into gas and liquid phases. When examined 5 hours after the commencement of the reaction, conversion of isopropanol was found to be 73 mole % and selectivity of propylene was 88 mole %. Diisopropyl ether was found as a byproduct.

Next, steam resistance of the comparative catalyst 1 was evaluated in accordance with the procedure described above. Results of the X-ray analysis of the comparative catalyst after its steam resistance test showed about 30% of transition into α-form.

A 40 cc portion of the comparative catalyst 1 after its steam resistance test was packed in the same type of reaction tube as used in Example 1, and the reaction was carried out under the same conditions as described in Example 1. A gas/liquid mixture discharged from the bottom of the reaction tube was separated into gas and liquid phases. When examined 5 hours after the commencement of the reaction, conversion of isopropanol was found to be 48 mole % and selectivity of propylene was 75 mole %, thus showing sharp decrease in the catalytic activity by the steam treatment. Diisopropyl ether was found as a byproduct.

Example 2

A vertical type reaction tube made of SUS 316 (inside diameter, 38.1 ram; length, 4,300 ram) equipped with an external oil bath was packed with 4,550 cc of the catalyst 1, and temperature of the oil bath was increased to 315° C. Isopropanol was fed from the top of the reaction tube at an LHSV of 1 $hr^{-1}$ and the reaction was effected by increasing pressure in the reaction tube to 18 kg/cm2G. A gas/liquid mixture discharged from the bottom of the reaction tube was separated into gas and liquid phases. When examined 10 hours after the commencement of the reaction, conversion of isopropanol was found to be 81 mole % and selectivity of propylene was 95 mole %. Diisopropyl ether was found as a byproduct. In addition, when examined 3,000 hours after the commencement of the reaction, conversion of isopropanol was found to be 80 mole % and selectivity of propylene was 94 mole %. When the catalyst after completion of the reaction was examined by X-ray analysis, formation of α-form was found in an amount of 1%. Thus, it was found that transition into α-form and decrease in the catalytic activity were negligible even after a prolonged period of reaction time.

Examples 3 and 4

The procedure of Example 2 was repeated using the same reaction tube under the same reaction conditions, except that the catalyst 1 was replaced by the catalysts 2 and 3 in Examples 3 and 4, respectively. The results are shown in Table 1.

Comparative Example 2

The procedure of Example 2 was repeated using the same reaction tube under the same reaction conditions, except that the catalyst 1 was replaced by the comparative catalyst 1. The results are shown in Table 1.

Example 5

The reaction tube used in Example 1 was packed with 40 cc of the catalyst 2, and temperature of the electric furnace was increased to 400° C. Ethanol was fed from the top of the reaction tube at an LHSV of 0 5 $hr^{-1}$ and the reaction was effected by increasing pressure in the reaction tube to 18 $kg/cm^2G$. A gas/liquid mixture discharged from the bottom of the reaction tube was separated into gas and liquid phases. When examined 5 hours after the commencement of the reaction, conversion of ethanol was found to be 83 mole % and selectivity of ethylene was 94 mole %. Diethyl ether was found as a byproduct.

Next, steam resistance of the catalyst 2 was evaluated in accordance with the procedure described above. Results of the X-ray analysis of the thus treated catalyst showed about 5% transition into α-form.

A 40 cc portion of the catalyst 2 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of ethanol was found to be 78 mole % and selectivity of ethylene was 92 mole %. Diethyl ether was found as a byproduct. (Example 6)

The reaction tube used in Example 1 was packed with 40 cc of the catalyst 3, and temperature of the electric furnace was increased to 300° C. Isobutanol was fed from the top of the reaction tube at an LHSV of 2 hr$^{-1}$ and the reaction was effected by increasing pressure in the reaction tube to 8 kg/cm$^2$G. A gas/liquid mixture discharged from the bottom of the reaction tube was separated into gas and liquid phases. When examined 5 hours after the commencement of the reaction, conversion of isobutanol was found to be 93 mole % and selectivity of isobutene was 96 mole %. Diisobutyl ether was found as a byproduct.

Next, steam resistance of the catalyst 3 was evaluated in accordance with the procedure described above. Results of the X-ray analysis showed no transition into γ-form.

A 40 cc portion of the catalyst 3 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of iosbutanol was found to be 93 mole % and selectivity of isobutene was 96 mole % thus showing no changes in the catalytic activity by the steam treatment. Diisobutyl ether was found as a byproduct.

Comparative Example 3

The reaction tube used in Example 1 was packed with 40 cc of the comparative catalyst 1, and temperature of the electric furnace was increased to 300° C. Isobutanol was fed from the top of the reaction tube at an LHSV of 2 hr$^{-1}$, and the reaction was effected by increasing pressure in the reaction tube to 8 kg/cm$^2$G. A gas/liquid mixture discharged from the bottom of the reaction tube was separated into gas and liquid phases. When examined 5 hours after the commencement of the reaction, conversion of isobutanol was found to be 74 mole % and selectivity of isobuten was 87 mole %. Diisobutyl ether was found as a byproduct.

Next, steam resistance of the comparative catalyst 1 was evaluated in accordance with the procedure described above. Results of the X-ray analysis showed about 30% transition into α-form.

A 40 cc portion of the comparative catalyst 1 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of isobutanol was found to be 52 mole % and selectivity of isobutene was 77 mole %. Diisobutyl ether was found as a byproduct.

Example 7

A vertical type reaction tube made of SUS 316 (inside diameter, 25.4 mm; length, 50 cm) equipped with an external electric furnace was packed with 40 cc of the catalyst 4, and temperature of the electric furnace was increased to 320° C. Isopropanol was fed from the top of the reaction tube at an LHSV of 1 hr$^{-1}$ and the reaction was effected by increasing pressure in the reaction tube to 18 kg/cm$^2$G. A gas/liquid mixture discharged from the bottom of the reaction tube was separated into gas and liquid phases. When examined 5 hours after the commencement of the reaction, conversion of isopropanol was found to be 90 mole % and selectivity of propylene was 92 mole %. Diisopropyl ether was found as a byproduct.

Next, steam resistance of the catalyst 4 was evaluated in accordance with the procedure described above. Results of the X-ray analysis showed no transition into α-form. A 40 cc portion of the catalyst 4 after its steam resistance test was packed in the same type of reaction tube as used in the above experiment, and the reaction was carried out under the same conditions as described in Example 7. A gas/liquid mixture discharged from the bottom of the reaction tube was separated into gas and liquid phases. When examined 5 hours after the commencement of the reaction, conversion of isopropanol was found to be 87 mole % and selectivity of propylene was 90 mole %. Diisopropyl ether was found as a byproduct Example 8

A vertical type reaction tube made of SUS 316 (inside diameter, 38.1 mm; length, 4,300 mm) equipped with an external oil bath was packed with 4,550 cc of the catalyst 4, and temperature of the oil bath was increased to 315° C. Isopropanol was fed from the top of the reaction tube at an LHSV of 1 hr$^{-1}$ and the reaction was effected by increasing pressure in the reaction tube to 18 kg/cm$^2$G. A gas/liquid mixture discharged from the bottom of the reaction tube was separated into gas and liquid phases. When examined 10 hours after the commencement of the reaction, conversion of isopropanol was found to be 89 mole % and selectivity of propylene was 95 mole %. Diisopropyl ether was found as a byproduct. In addition, when examined 3,000 hours after the commencement of the reaction, conversion of isopropanol was found to be 85 mole % and selectivity of propylene was 92 mole %. When the catalyst after completion of the reaction was examined by X-ray analysis, the catalyst was found totally as γ-form thus showing that transition of the catalyst into (x-form and decrease in the catalytic activity did not occur even after prolonged period of the reaction time.

Comparative Example 4

The reaction of Example 7 was repeated except that 40 cc of the comparative catalyst 2 was used. A gas/liquid mixture discharged from the bottom of the reaction tube was separated into gas and liquid phases. When examined 5 hours after the commencement of the reaction, conversion of isopropanol was found to be 73 mole % and selectivity of propylene was 88 mole %. Diisopropyl ether was found as a byproduct.

Next, steam resistance of the comparative catalyst 2 was evaluated in accordance with the procedure described above. Results of the X-ray analysis showed about 30% transition into α-form. Using the comparative catalyst 2 after its steam resistance test, the reaction was carried out using the same type of reaction tube and under the same reaction conditions as described in Example 7. A gas/liquid mixture discharged from the bottom of the reaction tube was separated into gas and liquid phases. When examined 5 hours after the commencement of the reaction, conversion of isopropanol was found to be 48 mole % and selectivity of propylene was 75 mole %. Diisopropyl ether was found as a byproduct. Thus, it was found that the comparative catalyst was transformed into α-form and its catalytic activity was reduced by the steam resistance test.

Comparative Example 5

The reaction of Example 7 was repeated except that 40 cc of the comparative catalyst 3 was used. A gas/liquid mixture discharged from the bottom of the reaction tube was separated into gas and liquid phases. When examined 5 hours after the commencement of the reaction, conversion of isopropanol was found to be 92 mole % and selectivity of propylene was 65 mole %. A heavy material was found as a byproduct. After 1,000 hours of the reaction, conversion of isopropanol was reduced to 43 mole %. The comparative catalyst after completion of the reaction showed no transition into $\alpha$-form, but its surface was covered with a large quantity of carbon.

Comparative Example 6

A vertical type reaction tube made of SUS 316 (inside diameter, 38.1 ram; length, 4,300 ram) equipped with an external oil bath was packed with 4,500 cc of the comparative catalyst 2, and temperature of the oil bath was increased to 315° C. Isopropanol was fed from the top of the reaction tube at an LHSV of 1 hr$^{-1}$, and the reaction was effected by increasing pressure in the reaction tube to 18 kg/cm$^2$G. A gas/liquid mixture discharged from the bottom of the reaction tube was separated into gas and liquid phases. When examined 10 hours after the commencement of the reaction, conversion of isopropanol was found to be 84 mole % and selectivity of propylene was 90 mole %. Diisopropyl ether was found as a byproduct. In addition, when examined 3,000 hours after the commencement of the reaction, conversion of isopropanol was found to be 54 mole % and selectivity of propylene was 84 mole %. When the comparative catalyst after completion of the reaction was examined by X-ray analysis, about 20% of transition into $\alpha$-form was found.

Example 9

A 40 cc portion of the catalyst 5 was packed in the reaction tube used in Example 7, and temperature of the electric furnace was increased to 400° C. Ethanol was fed from the top of the reaction tube at an LHSV of 0.5 hr$^{-1}$ and the reaction was effected by increasing pressure in the reaction tube to 18 kg/cm$^2$G. A gas/liquid mixture discharged from the bottom of the reaction tube was separated into gas and liquid phases. When examined 5 hours after the commencement of the reaction, conversion of ethanol was found to be 82 mole % and selectivity of ethylene was 95 mole %. Diethyl ether was found as a byproduct.

Next, steam resistance of the catalyst 5 was evaluated in accordance with the procedure described above. Results of the X-ray analysis showed no transition into $\alpha$-form. A 40 cc portion of the catalyst 5 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of ethanol was found to be 79 mole % and selectivity of ethylene was 91 mole %. Diethyl ether was found as a byproduct.

Comparative Example 7

A 40 cc portion of the comparative catalyst 2 was packed in the reaction tube used in Example 7, and the reaction was carried out under the same conditions as in Example 8. A gas/liquid mixture discharged from the bottom of the reaction tube was separated into gas and liquid phases. When examined 5 hours after the commencement of the reaction, conversion of ethanol was found to be 82 mole % and selectivity of ethylene was 94 mole %. Diethyl ether was found as a byproduct.

Next, steam resistance of the comparative catalyst 2 was evaluated in accordance with the procedure described above. Results of the X-ray analysis showed about 40% of transition into $\alpha$-form. A 40 cc portion of the comparative catalyst 2 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of ethanol was found to be 50 mole % and selectivity of ethylene was 79 mole %. Diethyl ether was found as a byproduct.

Example 10

A 40 cc portion of the catalyst 4 was packed in the reaction tube used in Example 7, and temperature of the electric furnace was increased to 300° C. Isobutanol was fed from the top of the reaction tube at an LHSV of 2 hr$^{-1}$ and the reaction was effected by increasing pressure in the reaction tube to 8 kg/cm$^2$G. A gas/liquid mixture discharged from the bottom of the reaction tube was separated into gas and liquid phases. When examined 5 hours after the commencement of the reaction, conversion of isobutanol was found to be 86 mole % and selectivity of isobutene was 92 mole %. Diisobutyl ether was found as a byproduct.

Next, steam resistance of the catalyst 4 was evaluated in accordance with the procedure described above. Results of the X-ray analysis showed no transition into $\alpha$-form. A 40 cc portion of the catalyst 4 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of isobutanol was found to be 83 mole % and selectivity of isobutene was 90 mole %. Diisobutyl ether was found as a byproduct.

Comparative Example 8

A 40 cc portion of the comparative catalyst 2 was packed in the reaction tube used in Example 7, and temperature of the electric furnace was increased to 300° C. Isobutanol was fed from the top of the reaction tube at an LHSV of 2 hr$^{-1}$, and the reaction was effected by increasing pressure in the reaction tube to 8 kg/cm$^2$G. A gas/liquid mixture discharged from the bottom of the reaction tube was separated into gas and liquid phases. When examined 5 hours after the commencement of the reaction, conversion of isobutanol was found to be 74 mole % and selectivity of isobutene was 87 mole %. Diisobutyl ether was found as a byproduct.

Next, steam resistance of the comparative catalyst 2 was evaluated in accordance with the procedure described above. Results of the X-ray analysis showed about 30% of transition into $\alpha$-form. A 40 cc portion of the comparative catalyst 2 after its steam resistance test was packed in the same type of reaction tube as used in the above experiment, and the reaction was carried out under the same conditions as described above. A gas/liquid mixture discharged from the bottom of the reaction tube was separated into gas and liquid phases. When examined 5 hours after the commencement of the reaction, conversion of isobutanol was found to be 52 mole % and selectivity of isobutene was 77 mole %. Diisobutyl ether was found as a byproduct.

TABLE 1-1

| No. | Inventive example 1 | | Comparative example 1 | | Inventive example 2 | | Inventive example 3 | | Inventive example 4 | | Comparative example 2 | |
|---|---|---|---|---|---|---|---|---|---|---|---|---|
| Material | isopropanol | | isopropanol | | isopropanol | | isopropanol | | isopropanol | | isopropanol | |
| Flow rate (hr$^{-1}$) | 1 | | 1 | | 1 | | 1 | | 1 | | 1 | |
| Temp. (°C.) | 300 | | 300 | | 315 | | 315 | | 315 | | 315 | |
| Pressure (kg/cm$^2$G) | 18 | | 18 | | 18 | | 18 | | 18 | | 18 | |
| Reaction time (hr) | 5 | 5 | 5 | 5 | 10 | 3000 | 10 | 3000 | 10 | 3000 | 10 | 3000 |
| Catalyst | 1 | after steam test | comparative catalyst 1 | after steam test | 1 | continuous operation | 2 | continuous operation | 3 | continuous operation | comparative catalyst 1 | continuous operation |
| α-form (%) | | 0 | | about 30 | | 1 | | 6 | | 0 | | about 20 |
| By-product | diisopropyl ether | | diisopropyl ether | | diisopropyl ether | | diisopropyl ether | | diisopropyl ether | | diisopropyl ether | |
| Alcohol conversion | 73 | 73 | 73 | 48 | 81 | 80 | 87 | 82 | 91 | 91 | 84 | 54 |
| Olefin selectivity | 92 | 88 | 75 | 95 | 95 | 94 | 96 | 95 | 97 | 97 | 90 | 84 |
| Olefin yield | 67 | 67 | 64 | 36 | 77 | 75 | 84 | 78 | 88 | 88 | 76 | 45 |

TABLE 1-2

| No. | Inventive example 5 | | Inventive example 6 | | Comparative example 3 | | Inventive example 7 | | Inventive example 8 | | Comparative example 4 | |
|---|---|---|---|---|---|---|---|---|---|---|---|---|
| Material | ethanol | | isobutanol | | isobutanol | | isopropanol | | isopropanol | | isopropanol | |
| Flow rate (hr$^{-1}$) | 0.5 | | 2 | | 2 | | 1 | | 1 | | 1 | |
| Temp. (°C.) | 400 | | 300 | | 300 | | 320 | | 315 | | 320 | |
| Pressure (kg/cm$^2$G) | 18 | | 8 | | 8 | | 18 | | 18 | | 18 | |
| Reaction time (hr) | 5 | 5 | 5 | 5 | 5 | 5 | 5 | 5 | 10 | 3000 | 5 | 5 |
| Catalyst | 2 | after steam test | 3 | after steam test | comparative catalyst 1 | after steam test | 4 | after steam test | 4 | continuous operation | comparative catalyst 2 | after steam test |
| α-form (%) | | 5 | | 0 | | about 30 | | 0 | | 0 | | 30 |
| By-product | diethyl ether | | diisobutyl ether | | diisobutyl ether | | diisopropyl ether | | diisopropyl ether | | diisopropyl ether | |
| Alcohol conversion | 83 | 78 | 93 | 93 | 74 | 52 | 90 | 87 | 89 | 85 | 73 | 48 |
| Olefin selectivity | 94 | 92 | 96 | 96 | 87 | 77 | 92 | 90 | 95 | 92 | 88 | 75 |
| Olefin yield | 78 | 72 | 89 | 89 | 64 | 40 | 83 | 78 | 85 | 78 | 64 | 36 |

TABLE 1-3

| No. | Comparative example 5 | | Comparative example 6 | | Inventive example 9 | | Comparative example 7 | | Inventive example 10 | | Comparative example 8 | |
|---|---|---|---|---|---|---|---|---|---|---|---|---|
| Material | isopropanol | | isopropanol | | ethanol | | ethanol | | isobutanol | | isobutanol | |
| Flow rate (hr$^{-1}$) | 1 | | 1 | | 0.5 | | 1 | | 2 | | 2 | |
| Temp. (°C.) | 320 | | 315 | | 400 | | 315 | | 300 | | 300 | |
| Pressure (kg/cm$^2$G) | 18 | | 18 | | 18 | | 18 | | 8 | | 8 | |
| Reaction time (hr) | 5 | 1000 | 10 | 3000 | 5 | 5 | 5 | 5 | 5 | 5 | 5 | 5 |
| Catalyst | comparative | continuous | comparative | continuous | 5 | after | comparative | after | 4 | after | comparative | after |

TABLE 1-3-continued

| No. | Comparative example 5 | | Comparative example 6 | | Inventive example 9 | Comparative example 7 | | Inventive example 10 | Comparative example 8 | |
|---|---|---|---|---|---|---|---|---|---|---|
| | rative cata-lyst 3 | nuous opera-tion | rative cata-lyst 2 | nuous opera-tion | steam test | rative cata-lyst 2 | steam test | steam test | rative cata-lyst 2 | steam test |
| α-form (%) | | 0 | | 20 | 0 | | 40 | 0 | | 30 |
| By-product | heavy material | | diisopropyl ether | | diethyl ether | diethyl ether | | diisobutyl ether | diisobutyl ether | |
| Alcohol conversion | 92 | 43 | 84 | 54 | 82  79 | 82 | 50 | 86  83 | 74 | 52 |
| Olefin selectivity | 65 | — | 90 | 84 | 95  91 | 94 | 79 | 92  90 | 87 | 77 |
| Olefin yield | 60 | — | 76 | 45 | 78  72 | 77 | 40 | 79  75 | 64 | 40 |

As has been described in the foregoing, according to the process of the present invention, lower olefins can be produced from lower alcohols with higher yield and higher selectivity for longer period of time in comparison with the prior art processes. The high purity lower olefins produced by the inventive process are useful as raw materials for use in the synthesis of various organic compounds and polymers.

We claim:

1. A process for producing a lower olefin at high conversion and at high selectivity by dehydrating a lower alcohol having 2 to 4 carbon atoms with an δ-alumina catalyst, wherein the dehydration is effected at a temperature in the range of from 150° to 500° C. under conditions such that the resulting olefin is in liquid state at an ordinary temperature, wherein said δ-alumina catalyst contains 0.3% by weight or less of impurities in total, excluding $SiO_2$, said impurities including 0.2% by weight or less of sulfur calculated in terms of $SO_4-$ and 0.03% by weight or less of sodium calculated in terms of $Na_2O$, wherein the proportion of the δ-alumina catalyst which has been converted to the α form after 3,000 hours of the dehydrating reaction is at most 1% by weight.

2. The process according to claim 1 wherein said δ-alumina catalyst is prepared from an organic aluminum compound.

3. In a method of reducing catalyst degradation in a catalytic process of producing a lower olefin by selectively dehydrating a C 1-4 lower alcohol at a temperature in the range of from 150° to 500° C. under conditions such that the resulting olefin is in liquid state at an ordinary temperature, the improvement wherein the catalyst is a γ-alumina catalyst containing at most 0.3% by weight of impurities in total, excluding $SiO_2$, said impurities including up to 0.2% sulfur calculated as $SO_4-$ and up to 0.03% by weight of sodium calculated in terms of $Na_2O$, and at the end of 3,000 hours of the dehydration reaction at most only 1% by weight is converted to the alpha form.

* * * * *